United States Patent [19]

Jacobs

[11] Patent Number: 5,538,948
[45] Date of Patent: Jul. 23, 1996

[54] METHOD FOR TREATING INFERTILITY COMPRISING ADMINISTERING GNRH ANALOG, GONADOTROPHINS, AND GROWTH HORMONE

[75] Inventor: Howard Jacobs, London, Great Britain

[73] Assignee: Novo Nordisk A/S, Bagsvaerd, Denmark

[21] Appl. No.: 328,970

[22] Filed: Oct. 24, 1994

Related U.S. Application Data

[63] Continuation of Ser. No. 777,395, filed as PCT/DK90/00133, May 31, 1990, abandoned.

[30] Foreign Application Priority Data

Jan. 30, 1987 [DK] Denmark .................................. 499/87
Jun. 2, 1989 [DK] Denmark .................................. 2729/89

[51] Int. Cl.$^6$ .......................... C07K 14/61; C07K 14/59; A61K 38/24; A61K 38/27
[52] U.S. Cl. .............................................. 514/12; 530/399
[58] Field of Search .......................... 514/2, 12; 424/562, 424/546; 530/399, 851

[56] References Cited

U.S. PATENT DOCUMENTS 4,255,420  3/1981  Bergfield .................................. 424/177

FOREIGN PATENT DOCUMENTS 0161063   11/1985  European Pat. Off. .
0300982    1/1989  European Pat. Off. .
WO88/01176  2/1988  WIPO .
WO88/05662  8/1988  WIPO .

OTHER PUBLICATIONS

Homberg et al. 1990 Fertility & Sterility 53:254.
Jia et al. 1986, Endocrinology 118(4): 1401.
Moretti et al. 1988 70fl Prog. & Abstracts of An Annual Meeting of the Endocrino Society p. 69, Abs. 195.
Word et al., Fertility and Sterility, vol. 54, No. 1, pp. 73–78 (1990).

Primary Examiner—Robert A. Wax
Assistant Examiner—K. Cochrane Carlson
Attorney, Agent, or Firm—Steve T. Zelson; Cheryl H. Agris

[57] ABSTRACT

A combination of GnRH analog, gonadotrophins, and growth hormone is very useful for treating infertility in higher mammals and humans since the probability of pregnancy is enhanced and the total doses of gonadotrophins are reduced. The treatment is initiated with administration of GnRH analog and continued with administration of gonadotrophins and growth hormone.

9 Claims, No Drawings

METHOD FOR TREATING INFERTILITY COMPRISING ADMINISTERING GNRH ANALOG, GONADOTROPHINS, AND GROWTH HORMONE

This application is a continuation of Ser. No. 07/777,395, filed as PCT/DK90/00133, May 31, 1990, now abandoned.

The present invention concerns a process for treating infertility in higher mammals or humans. The invention also concerns an agent for use in the process.

Higher mammals and humans of the female sex are born with a large number of oocytes. For women, the number of egg cells is about 200,000 in each ovary. After birth, many egg cells are lost before pubescence, and no new ones are formed.

The oocytes are surrounded by a ring of epithelial cells, so-called granulosa cells. The egg cell with the surrounding granulosa cells is called the follicle.

The ovarian function of higher mammals and humans is regulated by pituitary sex hormones, called gonadotrophins. These include the follicle stimulating hormone (FSH) which causes follicle maturation, and the luteinizing hormone (LH) which causes ovulation.

At the beginning of each menstrual cycle the ovaries are affected by the FSH hormone, so that a plurality of follicles grow, several layers of granulosa cells are being formed, and the follicle is also surrounded by cells formed from the surrounding tissue, the the cells.

Gradually, one follicle takes the lead, and the others degenerate. Normally, maturation of this one follicle takes 10 to 12 days. Also the amount of granulosa cells increases during the follicle maturation. Oestrogens are formed from these cells, and therefore increasing secretion of oestrogens will be a result of, and thus a measure of, the follicle maturation.

Halfway in the menstrual cycle the mature follicle bursts under the action of the LH released from the hypophysis, and the egg is discharged, ovulation. The egg passes out to the abdominal cavity and is caught by one Fallopian tube, through which it is conveyed to the uterus.

The follicle which has discharged the egg is transformed to a new hormone producing organ, the corpus luteum. Corpus luteum develops fully during the following days and produces progesterone together with oestrogens. Since progesterone is produced only in the corpus luteum, detection of progesterone implies ovulation with formation of a corpus luteum.

Corpus luteum has a limited life of about 12–14 days. Then, it very quickly ceases functioning, and the blood content of oestrogens and progesterone drops abruptly. This decline causes necrosis of the lining of the uterus, and menstruation usually occurs 13 to 14 days after the ovulation.

The production and release of FSH and LH by the pituitary is controlled partly from hypothalamus (a part of the brain positioned just above the pituitary) by release of gonadotrophin releasing hormone (GnRH) and partly via a feed-back mechanism conditional upon the oestrogen production in the ovaries.

Release and activity of GnRH is modified by a so-called negative feed-back mechanism. Increased oestrogen production and thus increased oestrogen concentration in the blood take place in step with the follicle maturation. The increased oestrogen concentration impairs (i.e. has a negative effect on) secretion of GnRH from hypothalamus and FSH and LH from the pituitary gland. Correspondingly, low oestrogen concentrations do not impair the GnRH secretion.

The causes of infertility in women include:

1) Abnormal ovarian function (primary ovarian failure)
2) Reduced hypothalamic-pituitary function, i.e. pituitary insufficiency, causing ovulatory failure (Secondary ovarian failure)
3) Tubal damage (adhesions, obstruction, etc).
4) Endometriosis (the presence of membranous material of the kind lining the uterus at other sites within the cavity of the pelvis)
5) Unexplained infertility.

Injections of gonadotrophins are used to treat infertility caused by pituitary insufficiency (in vivo fertilisation). Usually, in the case of absent ovulation, first, daily injections are administered with preparations having FSH activity, such as menotrophin, until a pre-ovulation oestrogen content in urine or plasma can be detected. Then, one or two injections of chorionic gonadotrophin are administered, which cause ovulation and the formation and function of a corpus luteum.

The use of gonadotrophin preparations is not a certain method of treating infertility. About 10–15% of the treated women do not respond to this treatment. Further, the treatments involve a considerable risk, because hyperstimulation easily occurs, which may cause big ovarian cysts, liquid or blood accumulations in the abdominal cavity and liquid accumulation in the thoracic cavity. Further, there is a risk of multiple pregnancy (twins, triplets, quadruplets, etc.).

From WO88/05662 it is known that growth hormones have a synergistic effect on gonadotrophins to stimulate ovarian function. Thus, a combination of gonadotrophins and human growth hormone is useful for treating infertility. However, infertility treatment in women with e.g. polycystic ovaries (PCO) is very difficult to handle. Women with PCO and being very resistant to treatment with gonadotrophins alone have demonstrated to respond to in vivo infertility treatment with a combination of gonadotrophins and growth hormone.

In women with PCO and not being resistant to the treatment for ovulation induction, it is very difficult to handle the treatment. The balance between giving enough but not too much of the stimulation treatment is very narrow and the risk of hyperstimulation is very high.

Recently a combination of GnRH analogue and gonadotrophins has been introduced as a new way of ovulation induction treatment for women with PCO.

Although such a combination does improve the probability for obtaining pregnancy significantly for women with PCO undergoing in vivo fertilisation and for women undergoing in vitro fertilisation (IVF), the preparation does not solve the infertility problem totally as only a limited increase of the probability for obtaining pregnancy is obtained. The present invention has been developed for further and decisive improvement of the infertility treatment.

It is known that GnRH analogues like buserelin inhibits the production of mature oocytes, and that the ovarian response may be provoked with gonadotrophins, so that multiple follicular growth (i.e. in vitro fertilisation) may occur, cf. de Zigler et al., Fertility and Sterility, vol. 48, No. 5, November 1987, p. 807–810. The same kind of treatment with GnRH analogues and gonadotrophins can also be used for unifollicular development (i.e. in vivo fertilisation).

The present invention is especially apt to be used for in vitro fertilisation (IVF) but is also very suitable for in vivo fertilisation. Succesful IVF requires multifollicular development (superovulation). Successful in vivo fertilisation is development of only one follicle—unifollicular development. Up to now it has been valid for both kinds of treatment that ovarian stimulation is obtained with the use of LMG or FSH alone or a combination of both with such a balanced dose that the desired object multifollicular—or unifollicular development is obtained.

Gonadotrophin releasing hormone (GnRH) is secreted from the hypothalamus to stimulate the synthesis and release of gonadotrophins, i.e. follicle stimulating hormone (FSH) and luteinizing hormone (LH) from the pituitary gland. The gonadotrophins then stimulate the ovaries to produce oestrogens and follicular growth.

Continuous administration of GnRH analogues desensitizes and decreases the number of GnRH receptors and also the pulsatile secretion of GnRH. This results in a reversible state of hypogonadotrophic hypogonadism with very low—if any secretion of FSH, LH, and oestrogens (down regulation). LMG FSH or a combination of FSH and hMG is then initiated at the time of down regulation for induction of multiple follicular growth (IVF) or unifollicular growth (in vivo fertilisation).

However, multiple follicular growth or superovulation and unifollicular development are not achieved in all women, despite the use of increasing amounts of gonadotrophins.

The present invention is based on the surprising discovery that in a treatment for IVF or in vivo fertilisation with gonadotrophins the ovarian response is highly augmented when the gonadotrophins are combined with as well a GnRH analogue as growth hormone.

In this way, a dramatic increase of the probability for obtaining fertilized eggs in IVF is achieved in comparison with a treatment with either a combination of GnRH analogues and gonadotrophins or a combination of gonadotrophins and growth hormone.

For in vivo fertilisation and particularly in women with PCO an increased ovarian sensitivity is obtained when growth hormone is given in combination with GnRH analogues and gonadotrophins compared to a combination of GnRH analogue and gonadotrophins.

With the increased ovarian sensitivity a smaller amount of gonadotrophins is required for unifollicular development and the risk of hyperstimulation can be reduced.

Examples of useful GnRH analogues which may be either a GnRH analogue antagonist or a GnRH analogue agonist are buserelin, triptorelin and leuprolide acetate.

The gonadotrophins may be used in the form of the naturally occurring human menopausal gonadotrophin (hMG), (recovered from urine and containing equal amounts of FSH and LH), and/or the individual components thereof, FSH and LH, separately or in any combination desired. It is also possible to use biosynthetically produced FSH and LH separately or in mixtures.

The administration of the components may be by the intravenous, intramuscular or subcutaneous route. Other routes of administration which may establish the desired blood levels of the respective components are comprised by the present invention.

The invention also concerns an agent and a kit for the treatment of infertility in higher animals or humans, comprising a combination of GnRH analogue, growth hormone, and gonadotrophins.

In order to obtain multifollicular development in human individuals, the individual is preferably treated with 2–40 mg buserelin, 500–20000 IU gonadotrophins and 2–160 IU hGH, administered in a number of daily doses. The optimal amounts are 3–20 mg buserelin, 1000–12000 IU gonadotrophins and 12–144 IU hGH.

Since the addition of growth hormone to the GnRHanalogues/gonadotrophin therapy significantly augments the ovarian response, it is considered that these data offer a new approach to the stimulation of ovarian function by utilizing known endocrine effects to influence paracrine control of ovarian function. Application of these principles for induction of multifollicular ovulation for programmes of assisted fertility (IVF with embryo transfer, GIFT, ovum donation, etc.) has a considerable potential.

The treatment of humans in accordance with the invention is illustrated in the following example.

EXAMPLE 1

1. Patients 10 patients were selected, all of which had 1–9 previous unsuccessful attempts of treatment with a GnRH analogue (buserelin) and gonadotrophins for IVF and all previously responding poorly to this treatment.

2. Methods and Drugs

Long term GnRH analogue+gonadotrophin treatment:

a) Last pre-study cycle (before growth hormone was given): The GnRH analogue buserelin was injected daily for downregulation of the ovaries from mid luteal phase of the previous cycle. When the ovaries were downregulated i.e. low oestrogen level and no follicles≧10mm (measured by ultrasound), treatment with gonadotrophins (i.e. hMG) was initiated. The dose of hMG was individually adjusted according to ovarian response. When 3 or more follicles had a diameter≧17 mm (measured by ultrasound) human chorionic gonadotrophin (hCG) was administered. 35 hours later oocytes were recovered for fertilisation, and embryos (or oocytes) were transferred back 2–3 days later (or sooner if oocytes were transferred).

b) Growth hormone (GH) cycle (The combined GnRH analogue+gonadotrophin+GH): All patients received buserelin and hMG in the same individually adjusted daily doses as in their last pre-study cycle. B-hGH injections (NORDITROPIN®) were administered concomitantly with hMG, and were initiated on the first day of administration of hMG (i.e. when the ovaries were down-regulated). The total dose of GH was 144 IU given as either 12 IU daily for 12 injections or as 24 IU every second day for 6 injections.

Otherwise, the patients were treated in exactly the same way as in their previous last treatment cycle without GH.

Results

There was an overall very positive ovarian response to the combined treatment of GH and buserelin/hMG.

The number of follicles≧14 mm went up from 5.7 (in the last pre-study cycle without GH) to 6.3 when growth hormone was given. This is an increase of 0.6 follicles or 10%.

The number of oocytes (i.e. eggs) collected increased considerably from 4.1 eggs to 7.2 eggs when GH was given. That is an increase of 3.1 eggs–75% increase.

The number of embryos replaced also went up dramatically from 1.3 before GH was given to 2.4 with GH. This is an increase of 1.1 embryos–85% increase.

Most important: none of the patients had been able to become pregnant on their last pre-study treatment, but 6 out of the 10 patients–60% became pregnant on GH-treatment.

The number of ampules of gonadotrophins required was significantly reduced from 91.8 ampoules per cycle to 58.8 ampules per cycle when GH was added. That is a reduction of 33 ampoules per cycle~35%.

Also the required number of treatment days was reduced when GH was given, from 19.6 days to 14.6 days, i.e. a reduction of 5 days~25%.

Regarding the above, cf. Table 1.

EXAMPLE 2

Growth hormone+gonadotrophin (without GnRH analogue)

5 patients, being previously poor responders (i.e. requiring 3 or more ampules of hMG per day, having reduced oestrogen production and/or reduced number of follicles≧14 mm) to treatment with clomiphene (an antioestrogen component used to enhance the effect of hMG) and hMG for induction of ovulation in IVF, were all treated for one cycle with a combination of hMG and B-hGH.

The results of this combined treatment were as follows:

1) No increase in number of follicles≧17 mm, but an increase in number of follicles between 14–16 mm was observed.
2) Number of eggs collected was 2 and 4 in two patients, compared with none in all 5 patients in their last pre-study cycle without GH.
3) Number of embryos replaces was 1 and 3 compared with none replaced in the 1st pre-study cycle in all 5 patients.
4) 1 patient out of 5 became pregnant compared with none in the last pre-study cycle.

EXAMPLE 3

A woman with PCO undergoing in vivo fertilisation with a combination of GnRH analogue agonist (Decapeptyl®) and HMG for unifollicular development was treated for one cycle with a combination of Decapeptyl®+ hMG+ B-hGH (NORDITROPIN®).

Long term GnRH analogue (Decapeptyl®)+gonadotrophin treatment (but without GH)

Decapeptyl® was injected i.m. on day of a natural or induced menstruation. Ovarian function was followed by ultrasound on day 14 and then once weekly until completely down-regulated i.e. $E_2$ level<20 pg/ml and the ovaries quiescent. Then hMG injections were initiated with 1–2ampules i.m. per day. From day 6 of hMG stimulation, the dosage of hMG was adjusted individually by 1 ampoule per day every 5days according to $E_2$ level, and until a sufficient ovarian response was obtained. This "daily effective dose" was then maintained until the diameter of 1–3 follicles was>17 mm whereupon human chorionic gonadotrophin (hCG) was administered i.m.

Growth Hormone (GH) cycle (the combined GnRH analogue+gonadotrophin+GH)

The patient received Decapeptyl® and hMG as described above but in addition also 12 IU of B-hGH (NORDITROPIN®) per day im.m for 7 days, initiated same day as hMG.

Results

The number of ampoules of gonadotropines required was reduced from 45 ampoules per cycle to 34 ampoules per cycle when GH was added. This is a reduction of 11 ampoules per cycle~ 24% reduction.

The number of treatment days with hMG was reduced from 22 days to 18 days when GH was added. This is a reduction of 4 days~18%.

The woman had ovulated but did not became pregnant in the treatment cycle without GH. She ovulated and became pregnant at the GH cycle.

Conclusion

IVF

The addition of growth hormone to treatment with GnRH analoges and gonadotrophins in patients undergoing IVF has proved to be highly efficient.

A greater number of follicles was developed; the number of eggs collected and number of embryos replaced increased considerably, and, most important, the pregnancy rate increased most significantly.

None of the patients had been able to become pregnant in their previous cycle with buserelin and gonadotrophins, but 6 out of 10 patients became pregnant on the combined growth hormone/buserelin/gonadotrophin therapy.

Also the required dose of gonadotrophins was reduced significantly, and the length of the follicular phase of the cycle of 14.6 days, i.e. length of treatment with gonadotrophins, resembles the length of the physiological follicular phase, so growth hormone has also a very beneficial effect on the cycle length.

When B-hGH was co-administered with hMG and without GnRH analogue, an improved ovarian response was observed, but the addition of GnRH analogue for down-regulation of the ovaries before stimulation with hMG and B-hGH highly and very significantly improved the ovarian response with multifollicular development and significant improvement of the pregnancy rate. The combination of GnRH analogue+B-hGH+hMG is very favourable for sensitizing the ovaries.

2) In vivo fertilisation

The addition of growth hormone to treatment with GnRH analogues and gonadotrophins in patients with PCO and undergoing in vivo fertilisation has proved to sensitise the ovary. Less stimulation with HMG was required i.e. fewer ampoules of HMG was required and for a shorter period. This decreases the risk of hyperstimulation which is a large problem in PCO's. The patient became pregnant on the combined GnRH analogues-HMG-GH treatment which had not happened in her previous cycle.

TABLE 1

A comparison of GH cycles versus last pre-study cycles.

| Variable | Last pre-study cycle (mean values) | GH-cycle (mean values) | Difference/ reduction in | |
|---|---|---|---|---|
| | | | Numbers | Percent |
| Follicles ≧ 14 mm/day HCG | 5.7 | 6.3 | 0.6 | 10 |
| Oocytes collected | 4.1 | 7.2 | 3.1 | 75 |
| Embryos replaced | 1.3 | 2.4 | 1.1 | 85 |
| Dose of hMG-amps | 91.8 | 58.8 | 33.0 | 35 |
| Duration of Rx-days | 19.6 | 14.6 | 5.0 | 25 |
| Pregnancies | 0 | ·6 | | |

I claim:

1. A pharmaceutical composition for treating infertility comprising a combination of gonadotrophins, a gonadotrophin releasing hormone analog and growth hormone.

2. The pharmaceutical composition according to claim 1 in which said composition comprises 1000–12000 IU gonadotrophin, 3–20 mg gonadotrophin releasing hormone analog, in which said gonadotrophin releasing hormone analog is buserelin and 12–144 IU human growth hormone.

3. A method for treating infertility in a woman comprising administering to the woman first a gonadotrophin releasing hormone analog, and subsequently gonadotrophins and growth hormone, the gonadotrophin releasing hormone analog administered for a period sufficient to cause down regulation of the secretion of follicle stimulating hormone, luteinizing hormone, and estrogen, and all components administered in an amount effective to increase ovarian response in the woman.

4. The method according to claim 3 in which the gonadotrophins, the gonadotrophin releasing hormone analog and the growth hormone are administered to the woman via injection.

5. The method according to claim 4 in which 500–12000 IU gonadotrophin, 2–40 mg gonadotrophin releasing hormone analog and 2–160 IU human growth hormone are injected to the woman.

6. The method according to claim 4 in which 1000–12000 IU gonadotrophin, 3–20 mg gonadotrophin releasing hormone analog and 12–144 IU human growth hormone are injected to the woman.

7. The method according to claim 3 in which the gonadotrophin releasing hormone analog is selected from the group consisting of buserelin, triptorelin and leuprolide acetate.

8. The method according to claim 3 in which said combination is administered to a woman undergoing in vitro 9. The method according to claim 3 in which said combination is administered to a woman undergoin in vivo fertilization.

* * * * *